United States Patent
Nwaigwe

(10) Patent No.: US 9,938,069 B2
(45) Date of Patent: Apr. 10, 2018

(54) MEDICAL DEVICE SANITIZER

(71) Applicant: Casmiar Nwaigwe, Minot, ND (US)

(72) Inventor: Casmiar Nwaigwe, Minot, ND (US)

( * ) Notice: Subject to any disclaimer, the term of this patent is extended or adjusted under 35 U.S.C. 154(b) by 62 days.

(21) Appl. No.: 14/846,365

(22) Filed: Sep. 4, 2015

(65) Prior Publication Data
US 2017/0066585 A1 Mar. 9, 2017

(51) Int. Cl.
| | | |
|---|---|---|
| *A61L 2/22* | (2006.01) | |
| *B65D 83/38* | (2006.01) | |
| *B65D 83/14* | (2006.01) | |
| *B05B 1/14* | (2006.01) | |
| *B65D 83/20* | (2006.01) | |
| *B65D 83/40* | (2006.01) | |

(52) U.S. Cl.
CPC .............. *B65D 83/386* (2013.01); *A61L 2/22* (2013.01); *B05B 1/14* (2013.01); *B65D 83/206* (2013.01); *B65D 83/384* (2013.01); *B65D 83/40* (2013.01); *B65D 83/752* (2013.01)

(58) Field of Classification Search
CPC .. B65D 83/384; B65D 83/386; B65D 83/752; A61L 2/22; A61B 90/70; B05B 9/03
See application file for complete search history.

(56) References Cited

U.S. PATENT DOCUMENTS

| | | | |
|---|---|---|---|
| 3,342,544 A | 9/1967 | Curiel | |
| 3,699,984 A | 10/1972 | Davis | |
| 6,253,773 B1 * | 7/2001 | Ingemann | ................. A47K 1/09 132/308 |
| 7,807,102 B1 | 10/2010 | Rezaizadeh et al. | |
| 8,931,494 B2 | 1/2015 | Weis et al. | |
| 2009/0144918 A1 * | 6/2009 | Perlman | ................. A61B 90/70 15/97.1 |
| 2014/0183193 A1 * | 7/2014 | Hammond | ............. B65F 1/002 220/87.2 |
| 2014/0186219 A1 | 7/2014 | Yukimoto | |
| 2014/0186221 A1 * | 7/2014 | Yukimoto | ................. A61L 2/24 422/111 |

* cited by examiner

*Primary Examiner* — David G Cormier
(74) *Attorney, Agent, or Firm* — Plager Schack LLP

(57) ABSTRACT

Some embodiments of the present disclosure include a sanitizing device for sanitizing a medical device. The sanitizing device may include a spray canister configured to accommodate a volume of a sanitizing fluid, the spray canister having at least one spray head extending therefrom, wherein the spray head is configured to expel sanitizing fluid when depressed; a body with an openable lid, the body configured to accommodate the spray canister, wherein a distance between an upper surface of the spray canister and an interior surface of the lid is sufficient to accommodate the medical device; and a lid protrusion extending downwardly from an interior surface of the lid, wherein the lid protrusion aligns with the spray head when the spray canister is positioned within the body. When the lid is closed, the lid protrusion may depress the spray head, resulting in the sanitizing fluid being expelled from the spray head.

8 Claims, 4 Drawing Sheets

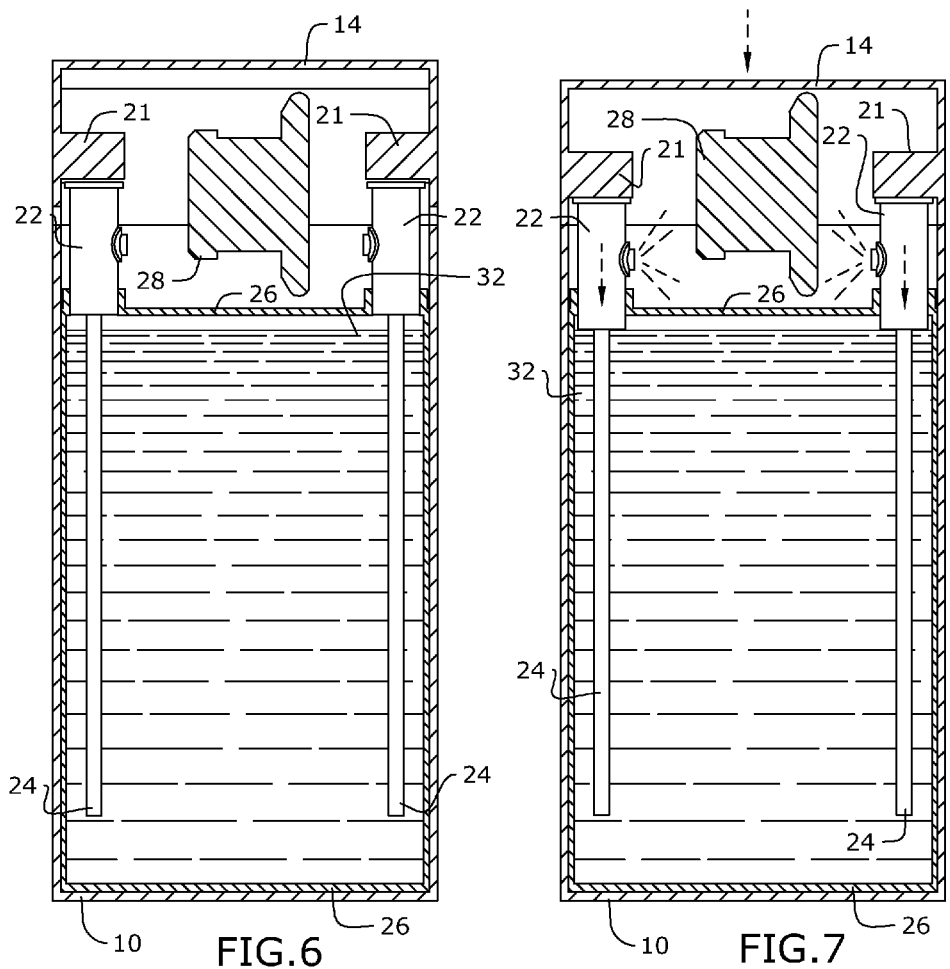

MEDICAL DEVICE SANITIZER

BACKGROUND

The embodiments herein relate generally to medical devices, and more particularly, to a sanitizer for medical devices, such as stethoscopes.

Medical devices that are used regularly throughout the day, such as stethoscopes, pick up germs from patients each time they are used. Currently, while doctors may wipe their devices down with alcohol wipes or other disinfectants after multiple uses, doctors do not typically sanitize their stethoscopes or many other regularly used devices between patients.

Therefore, what is needed is an easily-used device for sanitizing stethoscopes and other medical devices that are used on the skin in between patients.

SUMMARY

Some embodiments of the present disclosure include a sanitizing device for sanitizing a medical device. The sanitizing device may include a spray canister configured to accommodate a volume of a sanitizing fluid, the spray canister having at least one spray head extending therefrom, wherein the spray head is configured to expel sanitizing fluid when depressed; a body with an openable lid, the body configured to accommodate the spray canister, wherein a distance between an upper surface of the spray canister and an interior surface of the lid is sufficient to accommodate the medical device; and a lid protrusion extending downwardly from an interior surface of the lid, wherein the lid protrusion aligns with the spray head when the spray canister is positioned within the body. When the lid is closed, the lid protrusion may depress the spray head, resulting in the sanitizing fluid being expelled from the spray head.

BRIEF DESCRIPTION OF THE FIGURES

The detailed description of some embodiments of the invention is made below with reference to the accompanying figures, wherein like numerals represent corresponding parts of the figures.

FIG. 6 is a section view of one embodiment of the present disclosure, taken along line 6-6 in FIG. 4.

FIG. 7 is a section view of one embodiment of the present disclosure, taken along line 7-7 in FIG. 4.

DETAILED DESCRIPTION OF CERTAIN EMBODIMENTS

Figure 1:
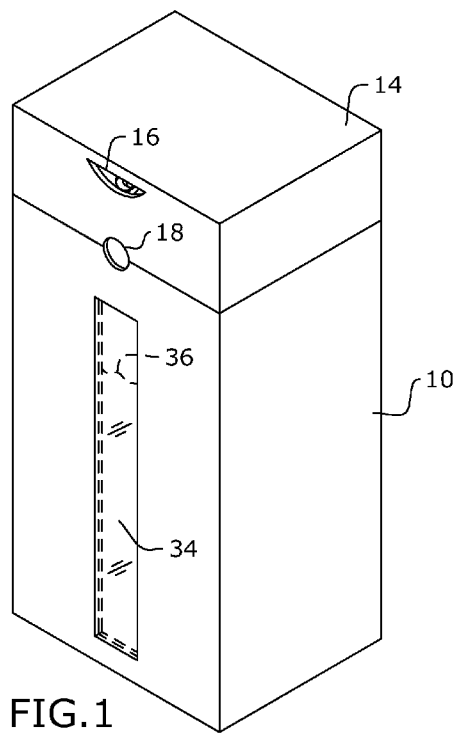
FIG. 1 is a perspective view of one embodiment of the present disclosure.
Figure 2:
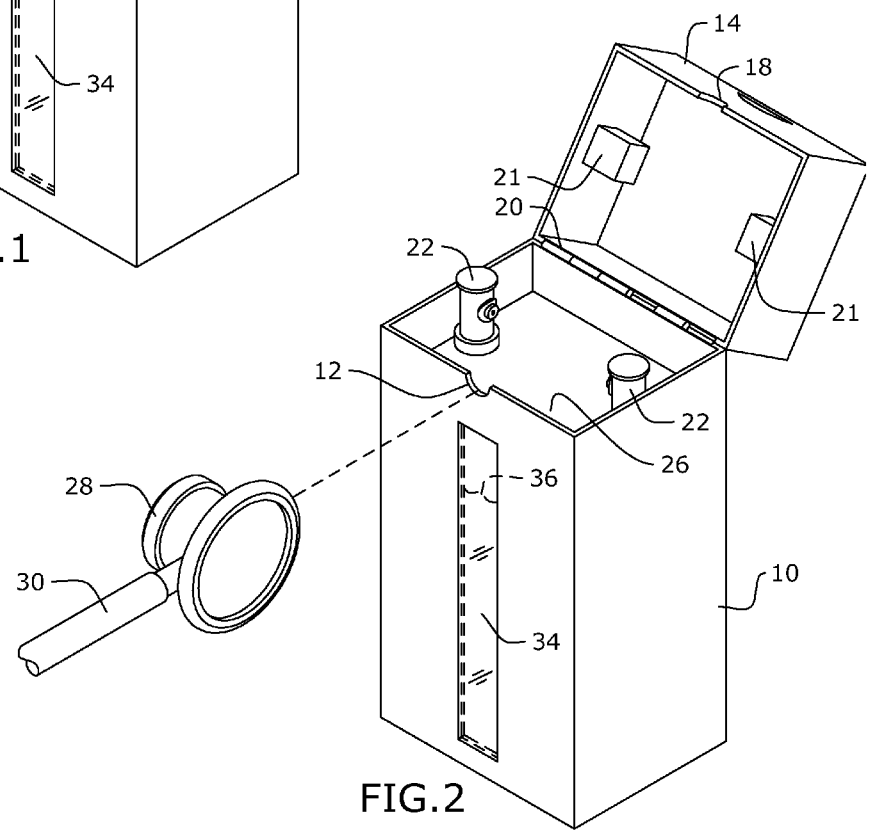
FIG. 2 is an exploded view of one embodiment of the present disclosure.
Figure 3:
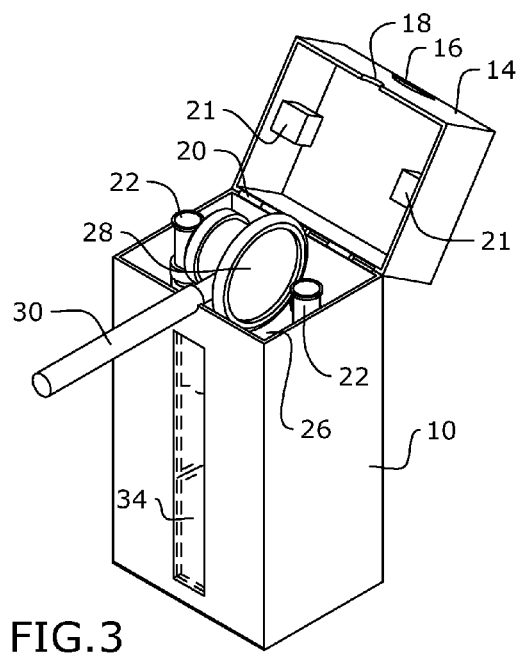
FIG. 3 is a perspective view of one embodiment of the present disclosure.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to sanitize a medical device and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Body
2. Openable Lid
3. Dispenser Canister

The various elements of the device for sanitizing a medical device of the present disclosure may be related in the following exemplary fashion. It is not intended to limit the scope or nature of the relationships between the various elements and the following examples are presented as illustrative examples only.

By way of example, and referring to FIGS. 1-8, some embodiments of the sanitizing device of the present disclosure comprise a body 10 with an openable lid 14, wherein the body 10 comprises an interior configured to accommodate a spray canister 26, such as a removable spray canister, wherein a distance between an upper surface of the spray canister 26 and an interior surface of the lid 14 is large enough to create an opening configured to accommodate a medical device, such as a stethoscope head 28. The spray canister 26 may comprise at least one spray head 22 extending from a surface thereof, wherein the spray head 22 is aligned with a corresponding lid protrusion 21 extending downwardly from an interior surface of the lid 14 towards the interior of the body 10, such that when the lid 14 is closed, the lid protrusion 21 is configured to depress the spray head 22, as shown in FIG. 7, resulting in a fluid 32, such as a sanitizing fluid, being expelled from the spray head 22. In some embodiments, the device comprises multiple spray heads 22, such as a pair of spray heads 22, wherein a space between the spray heads 22 is sufficient to accommodate a stethoscope head 28.

As shown in the Figures, the body 10 may comprise a body notch 12 that aligns with a lid notch 18 in the lid 14, such that when the lid 14 is closed, the body notch 14 and the lid notch 18 together form an orifice through which a portion of a medical device, such as a stethoscope tube 30 may extend. Thus, the device may accommodate just a portion of the medical device in a sanitizing area, wherein the sanitizing area is the area in the interior of the body 10 that comprises the spray head 22 and can accommodate the medical device. However, in other embodiments, the device may be configured to accommodate the entire medical device in the sanitizing area.

Figure 4:
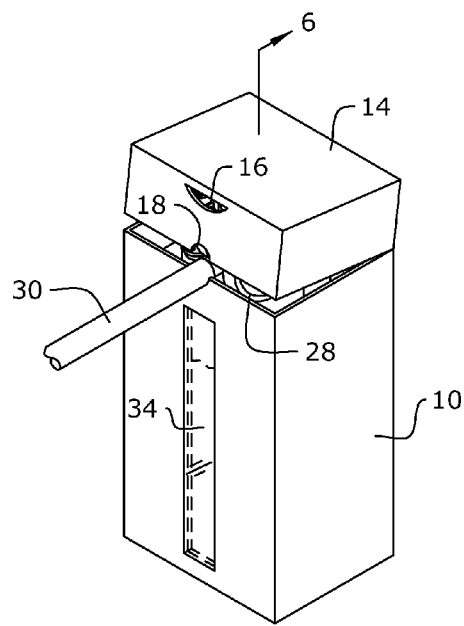
FIG. 4 is a perspective view of one embodiment of the present disclosure.
Figure 5:
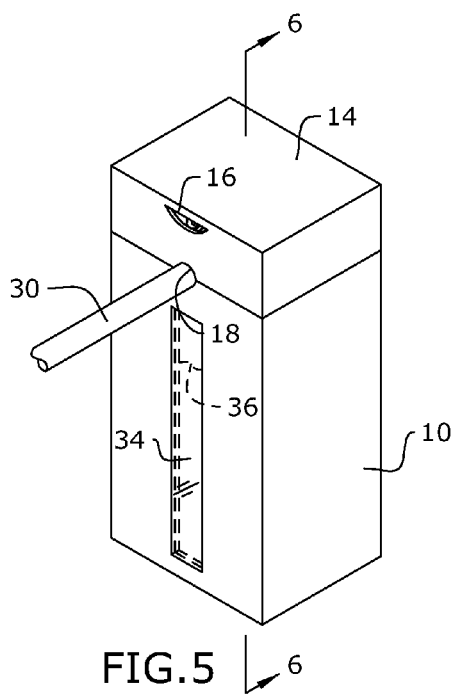
FIG. 5 is a perspective view of one embodiment of the present disclosure.

In embodiments, the lid 14 may also comprise a lid groove 16, wherein the lid groove 16 may aid a user in opening the lid 14. The lid 14 may also be hingeably attached to the body 10 via hinge 20. As shown in FIGS. 4 and 5, the lid 14 may have two closed configurations. In a first closed configuration, as shown in FIG. 4, the lid 14 may be substantially closed, but not depressed. In such a configuration, the lid groove 21 may not put pressure on the spray head 22 and, thus, may not cause the spray head 22 to expel fluid 32. In a second closed configuration, as shown in FIG. 5, the lid 14 may be completely closed, wherein the lid groove 21 does put pressure on the spray head 22, causing the spray head 22 to expel fluid.

Figure 8:
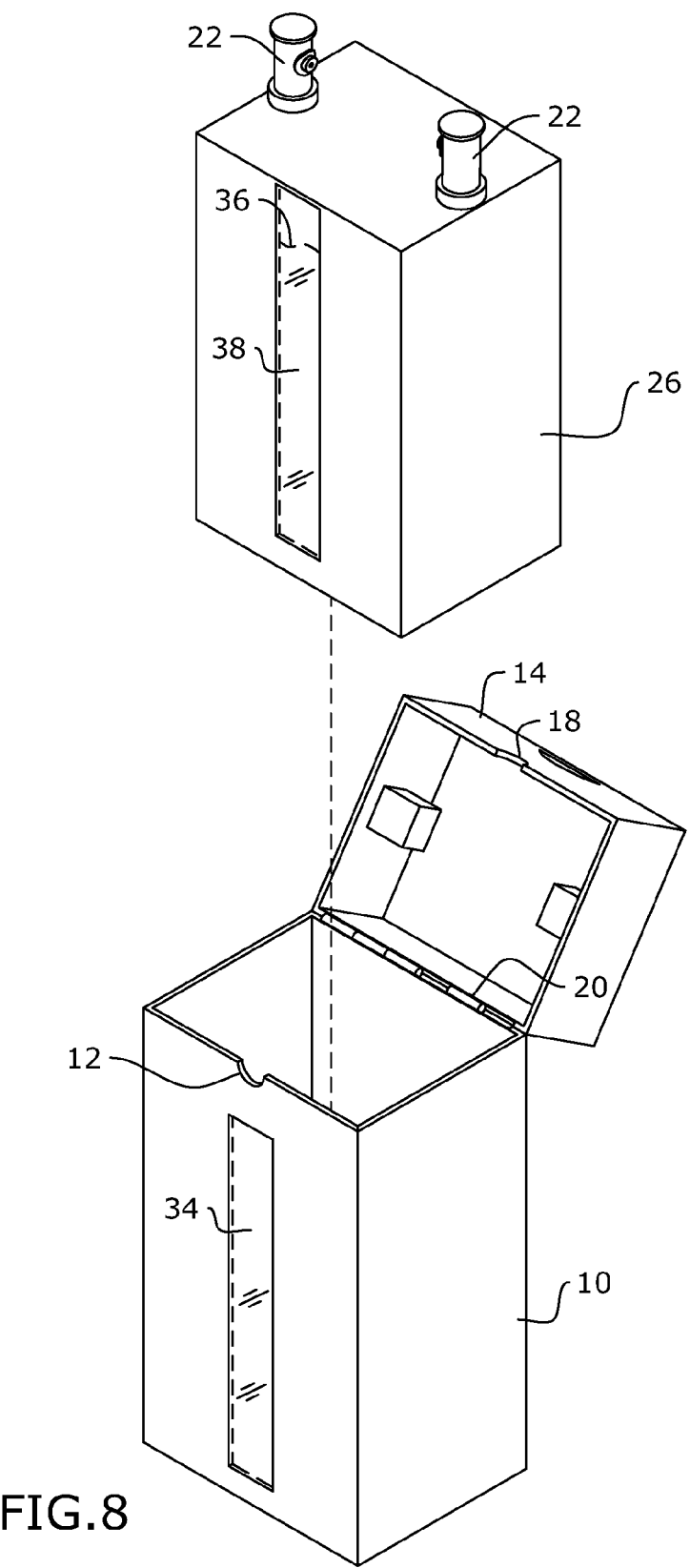
FIG. 8 is an exploded view of one embodiment of the present disclosure.

As shown in FIGS. 6-8, the spray canister 26 may comprise a canister configured to accommodate a volume of fluid 32, wherein at least one spray head 22 extends from a surface of the canister. The spray head 22 may be operatively attached to a spray tube 24 that extends downward into an interior of the spray canister 26, wherein the spray tube 24 is at least partially submerged in the fluid 32 when the spray canister 26 comprises a volume of fluid 32. In some embodiments, the spray tube 24 may extend to an area proximate to a surface of the canister opposite from the surface from which the spray head 22 extends. When the spray head 22 is depressed, fluid 32 may be pulled upwardly through the spray tube 24 into the spray head 22 and out of spray orifices in the spray head 22, thus expelling fluid 32 onto the medical device.

In some embodiments, each of the body 10 and the spray canister 26 may comprise a window through which a user can see into the interior of the device. The window 34 on the body 10 may align with a canister window 38 on the spray canister 26, such that a user may view the liquid level 36 of the fluid 32 from the exterior of the device. Thus, a user may be able to simply glance at the device and know if the fluid 32 needs to be replenished or filled or if the spray canister 26 needs to be replaced, in the case of a disposable and replaceable spray canister 26.

In embodiments, the device may comprise a mounting fastener to mount the body 10 onto a vertical surface, such as a wall. In other embodiments, the device may simply be designed to be placed on a horizontal surface, such as a countertop or a desk.

The device of the present disclosure may further comprise a removable tray or canister (not shown) positioned within the device to collect any excess or runoff fluid 32 that has pooled up after use of the device. The removable tray or canister may provide a user with a way to easily remove runoff fluid 32, wherein the removable tray or canister may be removed, emptied, and repositioned within the device for subsequent uses.

The device of the present disclosure may have any desired shape and size and may be made of any desired material, such as aluminum or plastic. The fluid contained within the canister 26 may comprise any desired sanitizing or cleansing solution and, in some embodiments, comprises a solution comprising a mixture of about 70% alcohol in about 0.25% hypochlorite.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A sanitizing device for sanitizing a medical device, the sanitizing device comprising:
 a spray canister configured to accommodate a volume of a sanitizing fluid, the spray canister comprising at least one spray head extending from a surface of the spray canister, the at least one spray head configured to expel sanitizing fluid when depressed;
 a body with an openable lid hingeably attached to an upper portion of the body, the body comprising an interior configured to accommodate the spray canister, wherein:
  the body comprises a body notch that aligns with a lid notch in the lid;
  when the lid is closed, the body notch and the lid notch together form an orifice through which a portion of the medical device is configured to extend;
  a distance between an upper surface of the spray canister and an interior surface of the lid is sufficient to accommodate the medical device; and
  the at least one spray head extends past the upper portion of the body and is positioned proximate to the openable lid;
 a lid protrusion extending downwardly from an interior surface of the lid towards the interior of the body, wherein the lid protrusion is configured to align with the at least one spray head when the spray canister is positioned within the body, such that when the lid is closed, the lid protrusion is configured to depress the at least one spray head, resulting in the sanitizing fluid being expelled from the at least one spray head onto the medical device.

2. The sanitizing device of claim 1, wherein the medical device is a stethoscope and the orifice is sized to accommodate a stethoscope tube extending there through.

3. The sanitizing device of claim 1, wherein the at least one spray head is operatively attached to a spray tube that extends downward into an interior of the spray canister such that when the at least one spray head is depressed, the sanitizing fluid in the spray canister is pulled upwardly through the spray tube into and through the at least one spray head, thus expelling the sanitizing fluid out of the at least one spray head.

4. The sanitizing device of claim 1, wherein:
 the spray canister comprises a pair of spray heads;
 the lid comprises a pair of lid protrusions, each lid protrusion positioned to align with a corresponding spray head; and
 a distance between the at least one spray heads is sufficient to accommodate the medical device.

5. The sanitizing device of claim 1, wherein:
 the body comprises a body window;
 the spray canister comprises a spray window; and
 the body window and the spray window are aligned such that a user can view a liquid level of the sanitizing fluid in the spray canister from an exterior of the sanitizing device.

6. The sanitizing device of claim 1, wherein the spray canister is removable and disposable.

7. The sanitizing device of claim 1, wherein:
 a volume of the sanitizing fluid is contained within the spray canister; and
 the sanitizing fluid comprises a solution comprising a combination of alcohol in hypochlorite.

8. The sanitizing device of claim 1, wherein the body and the spray canister each have a rectangular cross-section.

* * * * *